(12) United States Patent
Sullivan et al.

(10) Patent No.: US 10,092,430 B2
(45) Date of Patent: Oct. 9, 2018

(54) BALLOON WITH MANDREL SUPPORT GUIDEWIRE

(71) Applicant: Micro Medical Solutions, Inc., Quincy, MA (US)

(72) Inventors: Gregory Sullivan, Quincy, MA (US); Stephen Griffin, San Jose, CA (US)

(73) Assignee: Micro Medical Solutions, Inc., Wilmington, MA (US)

( * ) Notice: Subject to any disclaimer, the term of this patent is extended or adjusted under 35 U.S.C. 154(b) by 0 days.

(21) Appl. No.: 15/115,522

(22) PCT Filed: Jan. 29, 2015

(86) PCT No.: PCT/US2015/013461
§ 371 (c)(1),
(2) Date: Jul. 29, 2016

(87) PCT Pub. No.: WO2015/116787
PCT Pub. Date: Aug. 6, 2015

(65) Prior Publication Data
US 2016/0354219 A1    Dec. 8, 2016

Related U.S. Application Data

(60) Provisional application No. 61/932,856, filed on Jan. 29, 2014, provisional application No. 62/055,712, filed on Sep. 26, 2014.

(51) Int. Cl.
*A61F 2/958* (2013.01)
*A61M 25/00* (2006.01)
*A61M 25/01* (2006.01)
*A61M 25/10* (2013.01)

(52) U.S. Cl.
CPC .......... *A61F 2/958* (2013.01); *A61M 25/0054* (2013.01); *A61M 25/0102* (2013.01); *A61M 25/104* (2013.01); *A61M 2025/0081* (2013.01); *A61M 2025/1063* (2013.01); *A61M 2025/1084* (2013.01)

(58) Field of Classification Search
CPC .......... A61M 25/0054; A61M 25/0053; A61M 25/0051; A61M 25/0102; A61M 2025/0063; A61M 25/0138; A61M 25/0147; A61M 2025/015; A61M 2025/1063; A61F 2/958
See application file for complete search history.

(56) References Cited

U.S. PATENT DOCUMENTS

| | | | | |
|---|---|---|---|---|
| 3,985,601 A | * | 10/1976 | Panagrossi | A61M 25/1027 156/229 |
| 4,301,803 A | * | 11/1981 | Handa | A61M 25/1029 600/435 |
| 5,411,477 A | * | 5/1995 | Saab | A61F 7/123 264/521 |
| 5,667,521 A | | 9/1997 | Keown | |

(Continued)

*Primary Examiner* — Thomas McEvoy
(74) *Attorney, Agent, or Firm* — Bay State IP, LLC

(57) ABSTRACT

A coil-reinforced medical device delivery mechanism including a stiff proximal end for enhanced pushability and a soft distal end, including a free floating tip portion, for increased maneuverability and decreased breakage. The system utilizes a non-compliant balloon mounted on a flexible, single lumen shaft device with a support mandrel construction.

29 Claims, 6 Drawing Sheets

(56) References Cited

U.S. PATENT DOCUMENTS

| | | |
|---|---|---|
| 2005/0183729 A1 | 8/2005 | Fisher, Jr. |
| 2006/0100687 A1* | 5/2006 | Fahey .................. A61F 2/95 623/1.11 |
| 2008/0015625 A1* | 1/2008 | Ventura ............. A61B 17/3439 606/191 |

* cited by examiner

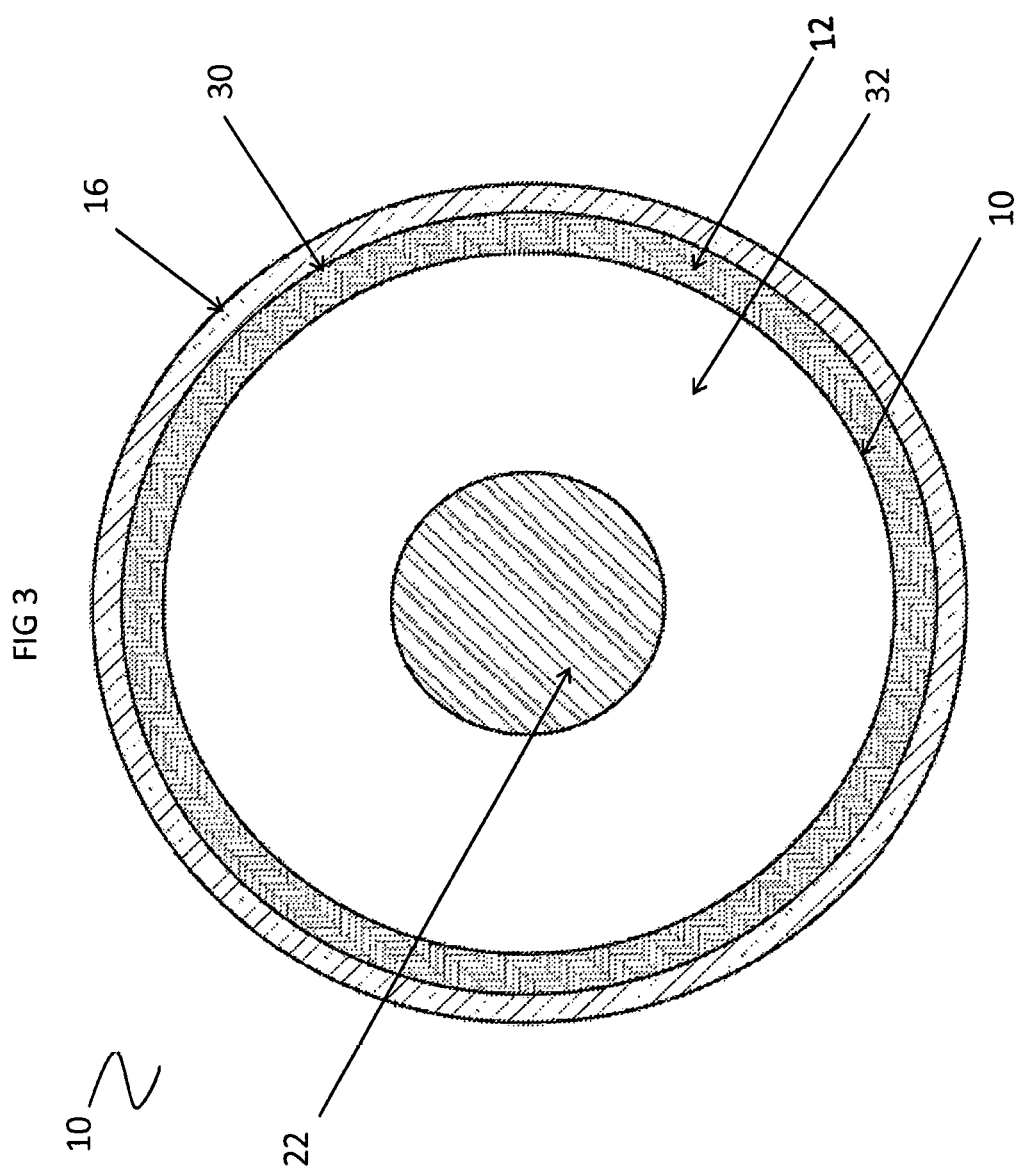

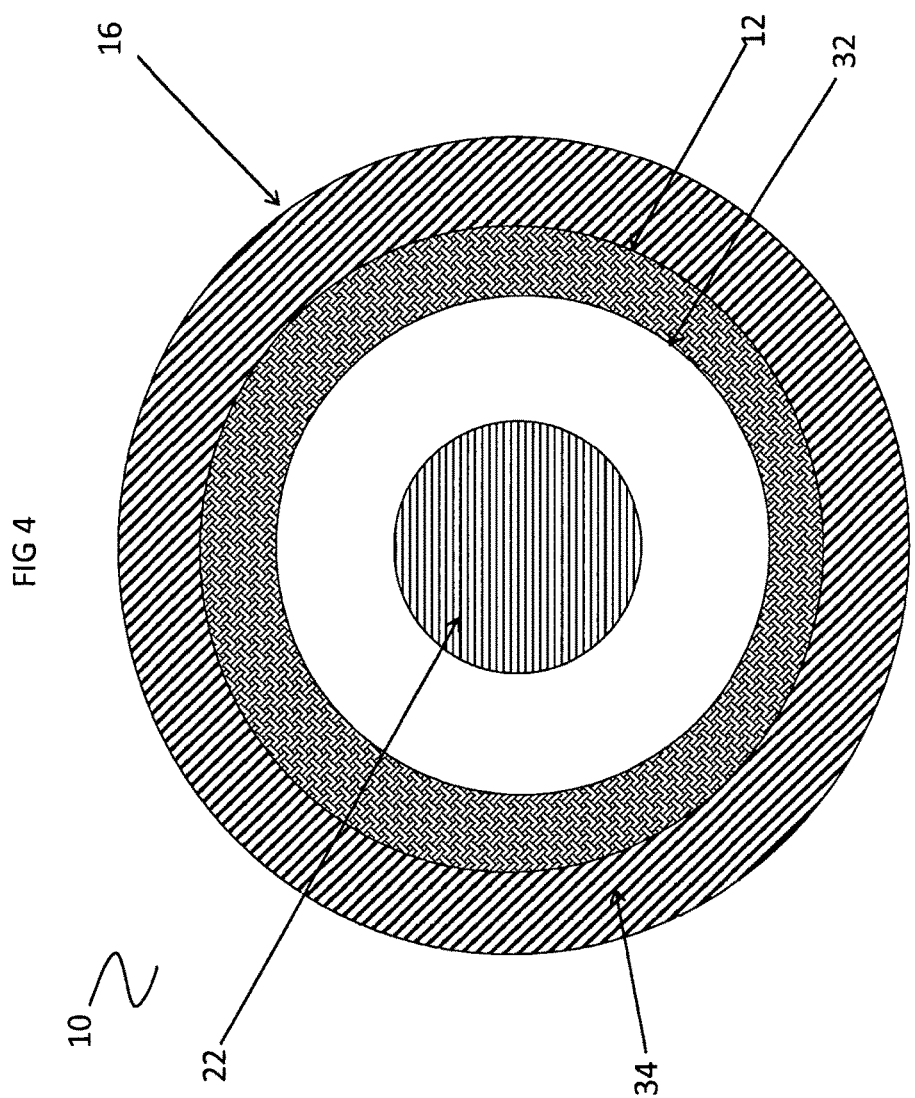

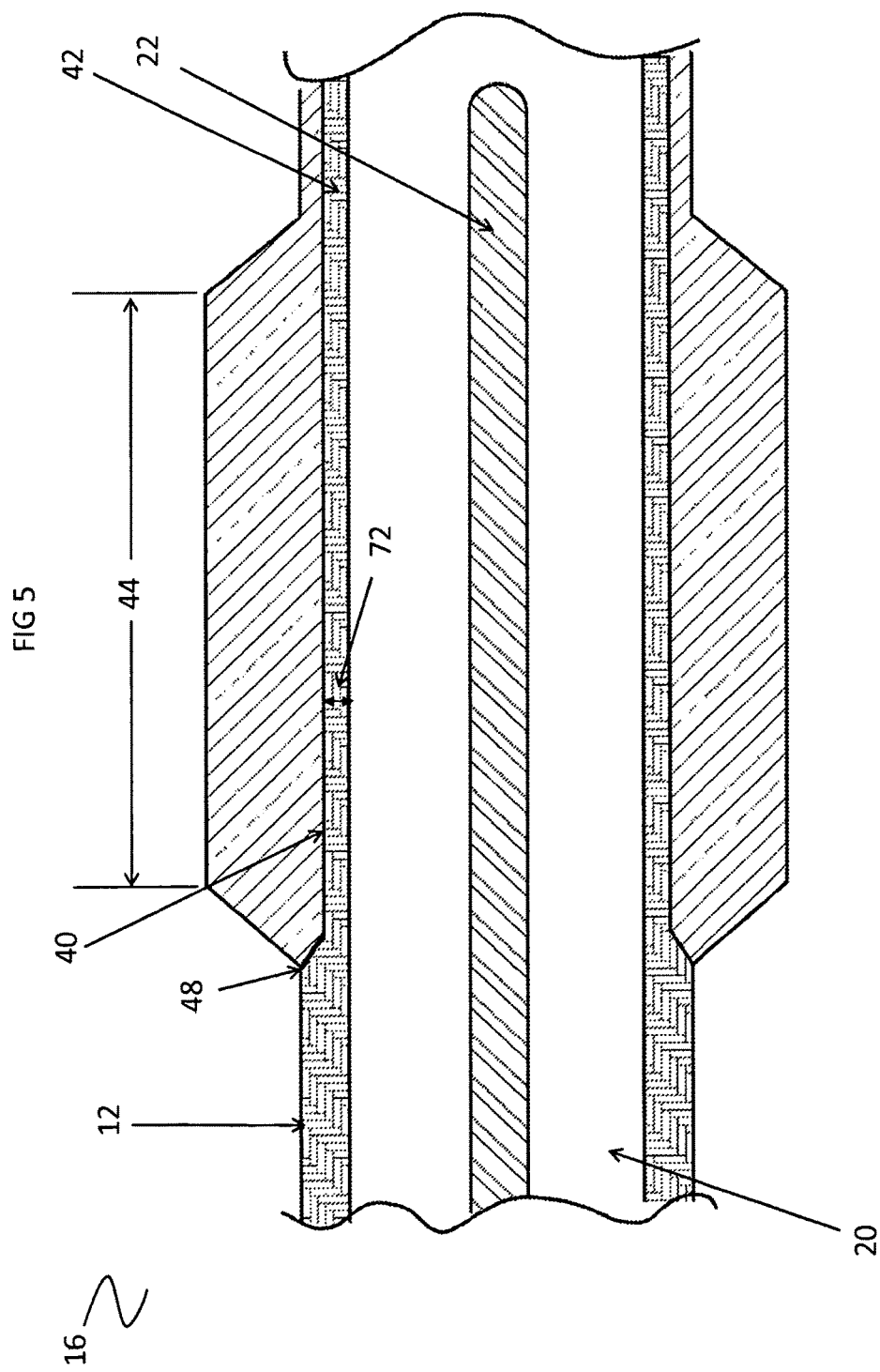

BALLOON WITH MANDREL SUPPORT GUIDEWIRE

CROSS REFERENCE TO RELATED APPLICATION

This application is for entry into the U.S. National Phase under § 371 for International Application No. PCT/US2015/013461 having an international filing date of Jan. 29, 2015, and from which priority is claimed under all applicable sections of Title 35 of the United States Code including, but not limited to, Sections 120, 363, and 365(c), and which in turn claims the benefit of and takes priority from U.S. App. No. 61/932,856 filed on Jan. 29, 2014, and U.S. Provisional Application No. 62/055,712, filed on Sep. 26, 2014, the contents of which are hereby incorporated by reference.

BACKGROUND OF THE INVENTION

Field of the Invention

The present invention pertains to medical devices and systems including the versatile system, method and series of apparatuses for creating and utilizing surgical stents and more specifically to a medical device delivery system and, in certain embodiments, particularly to systems and methods involving percutaneous coronary intervention (PCI), angioplasty and stenting.

Description of the Related Art

Arteriosclerosis, also known as atherosclerosis, is a common human ailment arising from the deposition of fatty-like substances, referred to as atheroma or plaque, on the walls of blood vessels. Such deposits occur both in the peripheral blood vessels that feed limbs of the body and coronary blood vessels that feed the heart. When deposits accumulate in localized regions of the blood vessels, blood flow is restricted and the person's health is at serious risk.

Of particular interest to the present invention are balloon angioplasty catheters having a balloon near its distal end for dilating the stenosed region. The angioplasty balloon catheter is then further advanced through the introducer sheath until the balloon passes beyond the distal end of the sheath and into the open vessel where it is aligned with the stenosed region. When the balloon is exposed to the stenosed region, the balloon is inflated to radially expand the vessel at the stenosed region. One particular drawback with such a treatment procedure is excessive vessel traumatization resulting from advancement and retraction of the balloon catheter within the vessel. Another drawback is that such a procedure usually requires the use of an elaborate angioplasty balloon catheter of the procedure. A further drawback is the time required to exchange catheters, thereby further increasing vessel trauma.

Intravascular balloon catheters, and the like, are often utilized in a wide variety of medical procedures to diagnose and treat vascular abnormalities such as aneurysms, stenotic lesions, intracranial shunts, etc. Such balloon catheters may be used for purposes of dilation, occlusion, flow control or tissue reformation.

Intravascular balloon catheters are typically navigated through the vasculature to the desired treatment site using a guide wire. The guide wire is insertable into the catheter and may be torqued to steer the distal end thereof and thereby direct the catheter into the desired vascular passage. Once in the desired position, the balloon may be inflated to treat the vascular abnormality. Such balloon catheters usually include a guide wire lumen shaft to accommodate the guide wire in addition to a separate inflation lumen shaft for inflating and deflating the balloon.

The provision of a guide wire lumen shaft separate from an inflation lumen dictates a catheter profile that may be too large for accessing relatively narrow vasculature often encountered, for example, in cranial applications. Accordingly, it is desirable to provide a combined guide wire lumen and inflation lumen to reduce the profile of the catheter and thereby enable access to narrow vasculature. Balloon catheters incorporating a combined guide wire lumen and inflation lumen are often referred to as "innerless" or "single lumen" balloon catheters.

A single lumen balloon catheter requires some sort of seal or valve between the guide wire and the catheter distal of the inflatable balloon. The seal is typically provided adjacent the distal end of the balloon and forms a close fit or an interference fit with the guide wire. Because of the close fit or interference fit, some friction between the guide wire and the seal may be encountered.

Due to the friction between the guide wire and the seal, in addition to the friction between the balloon and the vasculature, the balloon may be susceptible to longitudinal collapse. The tendency for longitudinal collapse is exasperated by the balloon structure which is usually formed of a thin flexible material.

To address the potential for longitudinal collapse, a support coil may be provided extending from the proximal end of the balloon to the distal end of the balloon adjacent the seal. The support coil provides column strength to the balloon and reduces the potential for longitudinal collapse.

Although the support coil provides column strength to the balloon, the transition in flexibility from the shaft immediately proximal to the balloon to the support coil within the balloon may be fairly abrupt. The support coil is inherently flexible and the balloon is very flexible since it is formed of a thin pliable material. The shaft, by contrast, is usually less flexible to provide sufficient pushability or ability to generate force to propel the apparatus to the desired destination within the subject's body. The result is an abrupt transition in stiffness from the relatively less flexible distal shaft portion to the relatively more flexible support coil and balloon. An abrupt transition in stiffness may translate into reduced trackability and an increased potential for kinking.

SUMMARY OF THE INVENTION

The instant apparatus and system, as illustrated herein, is clearly not anticipated, rendered obvious, or even present in any of the prior art mechanisms, either alone or in any combination thereof. In one embodiment, a versatile system, method and series of apparatuses is shown for the delivery of medical devices. Thus the several embodiments of the instant apparatus are illustrated herein.

The system, method and accompanying apparatuses relate generally to the field of medical devices and more particularly to field of vascular catheters, guide wires and hypotubes, and in particular to a mandrel support guidewire for delivering other diagnostic and/or therapeutic devices, having a compliant portion that can be radially expanded for therapeutic treatment of the vascular anatomy.

It is an object of the instant system to provide a system for utilization in percutaneous coronary intervention (PCI).

It is an object of the instant system to provide a system for the treatment of critical limb ischemia.

It is an object of the instant system to provide a coil-reinforced single lumen shaft.

It is a further object of the instant system to provide a low profile single lumen cut.

It is a further object of the instant system to provide for a mandrel support guidewire system.

It is an additional object of the instant system to provide for a single lumen shaft including a soft distal end to increase flexibility and reduce breakage.

It is an object of the instant invention to provide for a single lumen shaft with a low profile for easier maneuverability and more versatile insertion points.

It is an object of the instant invention to increase column strength through the use of a removable support mandrel.

It is an object of the instant invention to provide a guidewire with a dip-coated tip.

It is an object of the instant invention to provide for a coil-reinforced system wherein utilization of a hypotube is optional.

It is an object of the instant system to impart a non-compliant balloon mechanism mounted on a single lumen flexible shaft, which can be coiled or braided for reinforcement.

In one aspect, the present invention provides a new reinforced stent delivery system. Another aspect of the present invention provides a new reinforced stent delivery system, which includes a mandrel support system for increased stent precision and deployment.

Realizing one aspect of the system is a reinforced stent delivery system that is more accurate mechanism for stent delivery and deployment.

The subject system features a reinforced stent delivery system, which includes a reinforced single lumen that has a proximal end and a distal end. The system also includes a removably attached mandrel support guide wire with a thermally bonded balloon mechanism and a bonded tip. The bonded tip has a soft atraumatic tip attached to the balloon mechanism. Further, the thermally bonded balloon mechanism is bonded on the proximal side of the reinforced stent delivery system. The bonded tip is also free floating.

The distal head of the catheter is not directly affixed to the catheter body, which allows the distal head to move freely (or "float"), relative to the distal end of the catheter body. This freedom of movement generally provides increased efficiency of the catheter, therefore, less wear and tear and premature breakage.

The reinforced stent delivery system has a hypotube mechanism. The reinforced single lumen shaft of the reinforced stent delivery system has at least one cut portion and a stiff proximal end and a soft distal end. The reinforced stent delivery system proximal end diameter is equal to the diameter of the distal end. The one cut portion has a set of cut patterns located on different position throughout the length of the single lumen shaft to provide varying degrees of stiffness throughout the length of the single lumen shaft. The single lumen shaft also has a reinforced polymer outer layer within the interstices or spaces of the cut pattern. The reinforced polymer outer lay may be selected from the group consisting of PEBAX, Nylon, or polyurethane. The polymer outer layer is also 0.004 inches thick.

The catheter within the reinforced stent delivery system ranged from 1.5 French to 20 French. Further, the reinforced single lumen shaft has an interior cavity that is hollow and has a coating of Teflon. The outer surface of the reinforced single lumen shaft also tapers to a smaller outer diameter at the distal end. The balloon is thermally bonded to the leading edge of a taper of the outer surface approaching the edge of the outer surface. The purpose of the taper is to allow for the deflated balloon to lie flat creating a consistent outer diameter of the apparatus.

The consistent outer diameter further allows for ease of maneuverability during insertion of the reinforced single lumen shaft. The terminal end of the balloon is free floating and not bonded to the outer surface of the reinforced single lumen shaft. The terminal end of the balloon encompasses the entirety of the terminal end of the reinforced single lumen shaft. The bonded tip has a soft atraumatic bonded tip affixed to the balloon.

The subject invention also features a stent mechanism with a reinforced single lumen shaft with a proximal and a distal end, a removably attached mandrel support guidewire, a non-compliant balloon mounted on a single lumen shaft and a bonded tip. The non-compliant balloon has a coiled body and a braided body for reinforcement. The braided body has a nitinol braid and a platinum core and the strands of the braid are not intermingled. The non-compliant balloon mounted on the single lumen shaft may include a surface profile that may match the profile of a 0.018 guidewire.

The subject invention also features a medical device mechanism having a non-compliant balloon mounted on a flexible, single lumen shaft device which has a low profile, a sheath mechanism, and a removable support mandrel positioned inside the single lumen shaft device and the single lumen shaft device acts as a guidewire and a quantity of column strength for axial force is achieved by introducing the removable support mandrel inside the single lumen device for introducing through the sheath mechanism and tracking through the vessel of a patient.

The mandrel extends to the tip of the lumen, just beyond a distal balloon bond to the shaft and wherein the mandrel does not extend beyond the distal tip of the shaft as the lumen is sealed at the tip. The balloon device may be navigated to the target site, and then the support mandrel is removed leaving an inflation lumen for the balloon to be inflated. The single lumen shaft structure is selected from a group of structures consisting of coiled or braided for reinforcement purposes. The mandrel may include or be manufactured from a malleable material, in one embodiment a urethane material.

There has thus been outlined, rather broadly, the more important features of a medical device delivery system for protection during surgery embodiments in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

These together with other objects of the invention, along with the various features of novelty, which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

Advantages of the present invention and better understanding will be apparent from the following detailed description of exemplary embodiments thereof, which description should be considered in conjunction with the accompanying drawings, in which:

FIG. 3 is a front of a cross sectional view of the balloon comprising a mandrel support guidewire with the balloon deflated position;

FIG. 4 is a front of a cross sectional view of the balloon comprising a mandrel support guidewire with the balloon inflated position;

FIG. 5 is an exploded view of the balloon and balloon bonding area of the instant balloon comprising a mandrel support guidewire; and, FIG. 6A-6D are side views, partially in section, of the mandrel support guidewire stent system of FIG. 1 disposed within a patient's vessel, depicting a method of using the apparatus in accordance with the present invention.

DETAILED DESCRIPTION OF THE SEVERAL EMBODIMENTS

Embodiments of the present series of apparatuses, systems and interrelated methods pertain to a coil-reinforced stent use during angioplasty procedures. Throughout the description, for the purposes of explanation, numerous specific details are set forth in order to provide a thorough understanding of the present invention. It will be apparent, however, to one skilled in the art that the present invention may be practiced without some of these specific details. In other instances, well-known structures and devices are shown in generic form to avoid obscuring the underlying principles of the present invention.

Figure 1:
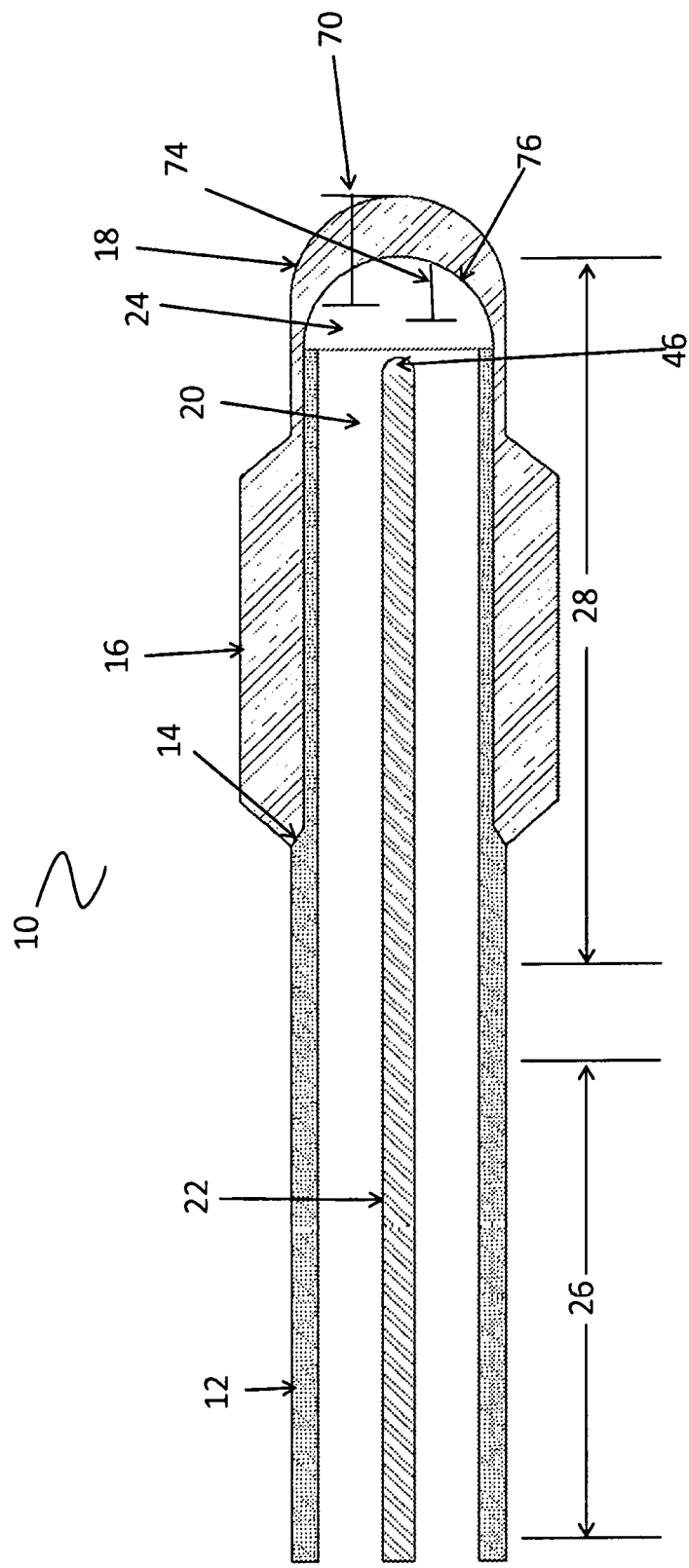
FIG. 1 is a side cross sectional view of the delivery system comprising a catheter with a mandrel support guidewire with the balloon in the inflated position.

FIG. 1 illustrates a side cross sectional view of a catheter 10 comprising a reinforced single lumen shaft with the removable mandrel support guidewire. The system may utilize a non-compliant balloon mounted on a single lumen shaft, which can be coiled or braided for reinforcement. The shaft profile may be manufactured to be low and flexible making it comparable to a guidewire. A desired measure of column strength for pushability is achieved by introducing a removable support mandrel inside this single lumen device for introducing through the sheath and tracking through the vessel. This mandrel extends to the tip of the lumen, just beyond the distal balloon bonded to the shaft. It does not however extend beyond the distal tip of the shaft as the lumen is sealed at the tip. Once the balloon device has been navigated to the target lesion, the support mandrel is removed leaving a patent inflation lumen for balloon inflation.

Moreover, the lower profile of the instant device is accomplished through the above described structure, featuring a single lumen device, which does not require both a balloon inflation lumen and guidewire lumen as in other such devices at the expense of profile.

In one embodiment, the catheter 10 generally comprises: a reinforced single lumen shaft 20; a removable mandrel support guidewire 22; a bonded balloon 16 that is inflated; the bonded balloon 16 may include a bonded tip 24 and an attached soft atraumatic tip 18. In one embodiment, the reinforced single lumen shaft 10 is comprised of a cut pattern providing for a stiff proximal end 26 and a soft distal end 28. In various other embodiments the cut pattern can provide varying degrees of stiffness throughout the length of the single lumen shaft 20.

Furthermore, a distal head 46 of the guidewire 22 preferably remains free-floating relative to an extreme distal end 70 of the catheter 10 but is anchored to the catheter 10 at a more proximal location (not shown). This anchoring helps ensure that the distal head 46 of the guidewire 22 will not break off from the catheter 10 during use. Any suitable anchoring device may be used and is contemplated within the scope of the invention.

Figure 2:
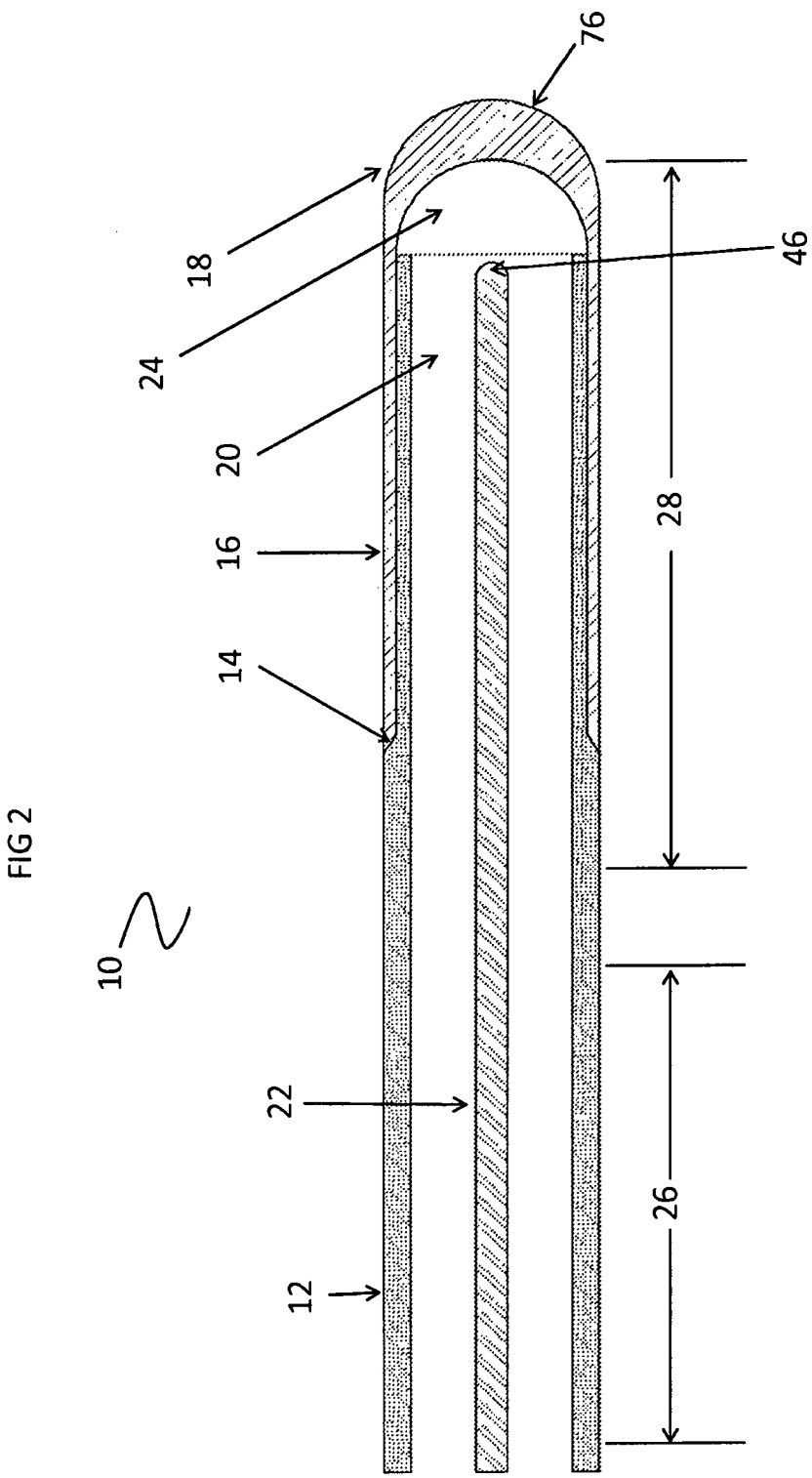
FIG. 2 is a side cross sectional view of the delivery system comprising a mandrel support guidewire with the balloon deflated position.

FIG. 2 illustrates a similar cross sectional view of the reinforced single lumen shaft 20 with the removable mandrel support guidewire 22, however, FIG. 2 further illustrates the bonded balloon 16 as deflated.

FIG. 3 illustrates front of a cross sectional view of the balloon 16 comprising a mandrel support guidewire 22 with the balloon 16 in deflated position 30. The reinforced single lumen shaft 20 is comprised of a reinforced polymer outer layer 12. The polymers may be selected from the group comprised of PEBAX, Nylon, or polyurethanes. In certain embodiments the reinforced polymer outer layer 12 comprises of a 0.004 inch wall. In other embodiments the reinforced polymer outer layer 12 wall thickness may be in a range of 0.0005 to 0.0015 inches. In certain embodiment an interior cavity 32 of the reinforced single lumen shaft 10 is comprised of a Teflon liner. The Teflon liner provides a smooth coating that reduces friction on the surface of the interior cavity.

Furthermore, the interior cavity 32 of the reinforced single lumen shaft 20 is substantially hollow. The reinforced single lumen shaft 20 is consistent in outer diameter from the proximal end 26 to the distal end 28. In the preferred embodiment the reinforced polymer outer layer 12 of the reinforced single lumen shaft 20 tapers 14 to a smaller outer diameter 72 substantially near the end of the distal end 28 of the reinforced single lumen shaft 20.

FIG. 4 illustrates a similar front cross section view of the balloon, however, FIG. 4 further illustrates the balloon 16 in an inflated position 34.

FIG. 5 illustrates a balloon 16 common to the art that is thermally bonded to a leading edge of the taper 48 of the polymer outer layer 12. The balloon 16 then extends along the tapered portion 40 of the polymer outer layer 12 approaching an end 42 of the tapered portion 40 the polymer outer layer 12. The taper 48 allows for a deflated balloon 16 to lie flat creating a consistent outer diameter of the catheter 10.

Additionally, the consistent outer diameter 72 of the catheter 10 when the balloon 16 is deflated allows for ease of maneuverability during insertion of the catheter 10 comprising the single lumen shaft 20 and the guidewire 22. In one embodiment, a terminal end 74 of the balloon 16 is not bonded to the polymer outer layer 12 of the reinforced single lumen shaft 20. The terminal end 74 of the balloon 16 encompasses the entirety of a terminal end 76 of the reinforced single lumen shaft 20. In the preferred embodiment a soft atraumatic bonded tip 18 is affixed to the terminal end 76 of the reinforced single lumen shaft 20.

The removable mandrel support guidewire 22 runs concentrically along a length of the reinforced single lumen shaft 20. In one embodiment, the guidewire 22 may be an intra-luminal mandrel support guidewire 22, which may be constructed with any number of materials and may be centerless ground to give a stiffness profile from the proximal end 26 to the distal end 28 of the single lumen shaft 20. Additionally, in another embodiment, the removable mandrel support guidewire 22 comprises a metal wire selected from the group consisting of: nitinol, cobalt chrome, and stainless steel.

In a preferred embodiment the mandrel support guidewire 22 is an elongated shaft with a selected flex profile along its length selected specifically for the intended use. The mandrel support guidewire 22 may be of a type common to the field of use. Furthermore, the mandrel support guidewire 22 preferably extends from the extreme proximal end 26 of the reinforced single lumen shaft 20 to the distal end 28. The distal head 46 of the mandrel support guidewire 22 extends just past the balloon shoulder 44 but not far enough to rupture the balloon 16. The soft distal end 28 of the single lumen shaft 20 allows for increased flexibility, which allows for increased maneuverability of a medical device; moreover, column strength for pushability may be achieved through the introduction of the mandrel support guidewire 22.

Moreover, in a preferred embodiment, the mandrel support guidewire 22 may be removable and not affixed to the single lumen shaft 20. The removability of the mandrel support guidewire 22 allows a user to preferably draw the mandrel support guidewire 22 from the reinforced single lumen shaft 20 to aide in the balloon 16 inflation.

In yet another embodiment, the lower stiffness profile of the delivery system may be accomplished as a single lumen shaft, instead of as in other devices, which require both a balloon inflation lumen and guidewire lumen, which in turn compromises the stiffness profile of the delivery system.

Figure 6A:
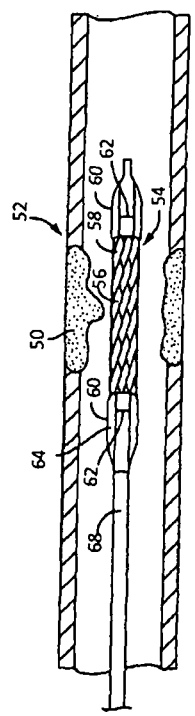

Referring to FIG. 6A, the distal end of the catheter 68 is delivered to a target site 50 within a patient's vessel 52. The guide wire 62 may facilitate positioning of system 54 at the target site. Alternatively, stent 58 or other portions of catheter 58 may be positioned as the user sees fit.

Figure 6B:
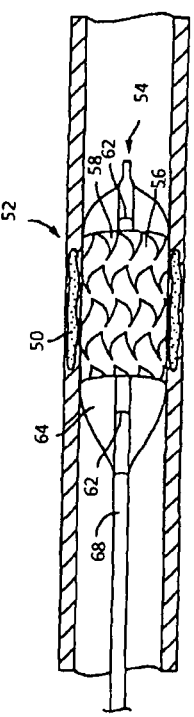
Figure 6C:
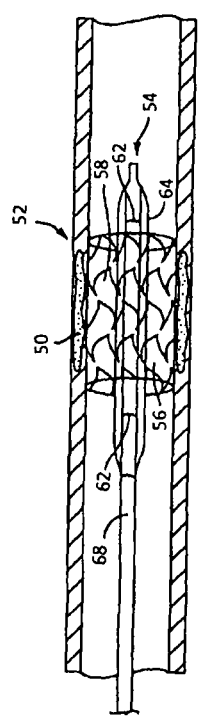
Figure 6D:
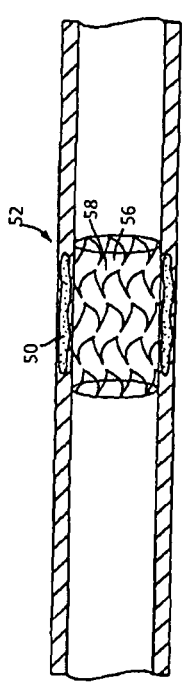

In FIG. 6B, balloon 64 is inflated, for example, via the lumen of the catheter 68. Stent 58 expands to the deployed configuration in which it contacts the wall of the vessel 52 at target site 50. Expansion of stent 58 opens interstices of the stent and removes the creases of balloon 64 from within the interstices. Additionally, stent 58 has a diameter in the deployed configuration that is larger than the diameter of the optional pillows 60, thereby facilitating removal of stent 58 from delivery catheter 68. Balloon 64 is then deflates, as shown in FIG. 6C, and delivery catheter 68 is removed from vessel 52, as seen in FIG. 6D.

Stent 58 remains in place within vessel 52 in the deployed configuration in order to reduce restenosis and recoil of the vessel. Stent 58 also may comprise a coating 56 to reduce the formation of thrombus or restenosis around the stent 58. Also, the coating 56 may deliver therapeutic agents into the patient's bloodstream or a portion of the vessel wall adjacent to the stent.

Although specific features of the invention are shown in some drawings and not in others, this is for convenience only as each feature may be combined with any or all of the other features in accordance with the invention. Other embodiments will occur to those skilled in the art and are within the following claims.

What is claimed is:

1. A reinforced stent delivery system comprising:
a catheter comprising a reinforced single lumen shaft, wherein the reinforced single lumen shaft further comprises a proximal end and a distal end and wherein a distal head of the catheter is not directly affixed to the reinforced single lumen shaft enabling the distal head to move freely relative to the distal end of the reinforced single lumen shaft;
a removably attached mandrel support guidewire anchored to the catheter at the proximal end and wherein a distal head of the mandrel support guidewire remains free-floating relative to an extreme distal end of the catheter;
a thermally bonded balloon mechanism;
a bonded tip;
wherein the single lumen shaft and the mandrel support guidewire both possess a variable stiffness profile throughout their respective lengths.

2. The reinforced stent delivery system of claim 1 wherein the bonded tip comprises a soft atraumatic tip affixed to the balloon mechanism.

3. The reinforced stent delivery system of claim 1 wherein the thermally bonded balloon mechanism is bonded on the distal end of the single lumen shaft.

4. The reinforced stent delivery system of claim 1 further comprising a hypotube mechanism.

5. The reinforced stent delivery system of claim 1 wherein the reinforced single lumen shaft comprises at least one cut pattern.

6. The reinforced stent delivery system of claim 5 wherein the at least one cut pattern comprises a set of cut patterns located throughout a length of the single lumen shaft to provide varying degrees of stiffness throughout the length of the single lumen shaft.

7. The reinforced stent delivery system of claim 6 wherein the single lumen shaft is comprised of a reinforced polymer outer layer.

8. The reinforced stent delivery system of claim 7 wherein the reinforced polymer outer layer is affixed into the interstices of the cut pattern.

9. The reinforced stent delivery system of claim 7 wherein the reinforced polymer outer layer comprises a material selected from the group consisting of PEBAX, Nylon, or polyurethanes.

10. The reinforced stent delivery system of claim 7 wherein the polymer outer layer comprises a .004 inch thick wall.

11. The reinforced stent delivery system of claim 1 wherein the reinforced stent delivery system comprises a stiff proximal end and a soft distal end.

12. The reinforced stent delivery system of claim 1, wherein the catheter is of a size in a range from 1.5French to 20 French.

13. The reinforced stent delivery system of claim 1 wherein the reinforced single lumen shaft comprises an interior cavity comprising a Teflon® coating.

14. The reinforced stent delivery system of claim 1 wherein a diameter of the proximal end is equal to a diameter of the distal end.

15. The reinforced stent delivery system of claim 1 wherein an outer surface of the reinforced single lumen shaft comprises a tapered portion which creates a smaller outer diameter at the distal end of the reinforced single lumen shaft.

16. The reinforced stent delivery system of claim 15 wherein the balloon is thermally bonded to a leading edge of a tapered portion of the outer surface of the reinforced single lumen shaft and wherein the balloon mechanism extends along the outer surface approaching the end of the outer surface.

17. The reinforced stent delivery system of claim 16 wherein the tapered portion of the outer surface of the reinforced single lumen shaft is disposed to retain the balloon mechanism in a deflated orientation which defines a consistent outer diameter of the apparatus wherein the consistent outer diameter allows for ease of maneuverability during insertion of the reinforced single lumen shaft.

18. The reinforced stent delivery system of claim 1 wherein a terminal end of the balloon mechanism is free floating and not bonded to an outer surface of the reinforced single lumen shaft.

19. The reinforced stent delivery system of claim 1 wherein the balloon mechanism comprises a terminal end and wherein the terminal end of the balloon mechanism encompasses the entirety of the distal end of the reinforced single lumen shaft.

20. The reinforced stent delivery system of claim 1, wherein the variable stiffness profile of the single lumen shaft matches the variable stiffness profile of the mandrel support guidewire.

21. The reinforced stent delivery system of claim 1, wherein the mandrel support guidewire is constructed from a metal wire selected from the group consisting of: nitinol, cobalt chrome and stainless steel.

22. A medical device mechanism comprising:
 a non-compliant balloon device mounted on a flexible, single lumen shaft device comprising a low profile;
 a sheath mechanism; and,
 a removable support mandrel positioned inside the single lumen shaft device wherein the single lumen shaft device acts as a guidewire;
 wherein the mandrel extends to a tip of the single lumen shaft device, just beyond a distal end of the non-compliant balloon device, and wherein the mandrel does not extend beyond a distal tip of the single lumen shaft device as the single lumen shaft device is sealed at the tip.

23. The medical device mechanism of claim 22 wherein when the non-compliant balloon device has been navigated to a target lesion, the support mandrel is removed leaving an inflation lumen for balloon inflation.

24. The medical device mechanism of claim 22 wherein the single lumen shaft device possesses a cut pattern for reinforcement selected from the group consisting of: coiled and braided.

25. The medical device mechanism of claim 24 wherein the non-compliant balloon comprises a body for reinforcement selected from the group consisting of braided and coiled.

26. The medical device mechanism of claim 25 wherein the body comprises a nitinol braid and a platinum core wherein the strands are not intermingled.

27. The medical device mechanism of claim 22 wherein the mandrel comprises a malleable material.

28. The medical device mechanism of claim 22 wherein the mandrel comprises a urethane material.

29. The medical device mechanism of claim 22 wherein the non-compliant balloon mounted on the single lumen shaft comprises a stiffness profile that matches a 0.018 guidewire.

* * * * *